United States Patent [19]

Sakamoto et al.

[11] 4,174,459

[45] Nov. 13, 1979

[54] PROCESS FOR PRODUCING METHACRYLIC ACID

[75] Inventors: Teruhisa Sakamoto; Taketoshi Nagahama; Shigeo Nakamura; Keiichi Kihara, all of Shin-nanyo, Japan

[73] Assignee: Toyo Soda Manufacturing Co., Ltd., Yamaguchi, Japan

[21] Appl. No.: 756,912

[22] Filed: Jan. 4, 1977

[30] Foreign Application Priority Data

Feb. 9, 1976 [JP] Japan .................................. 51/12245

[51] Int. Cl.² ....................... C07C 51/32; C07C 57/04
[52] U.S. Cl. .................................... 562/534; 252/435; 252/437; 562/535; 562/536
[58] Field of Search ................... 260/530 N; 252/435, 252/437; 562/534, 535

[56] References Cited

U.S. PATENT DOCUMENTS

| | | | |
|---|---|---|---|
| 3,875,220 | 1/1975 | White et al. | 260/530 N |
| 3,959,182 | 5/1976 | Izawa et al. | 260/530 N |

FOREIGN PATENT DOCUMENTS 2448804  4/1975  Fed. Rep. of Germany ...... 260/530 N

*Primary Examiner*—Vivian Garner
*Attorney, Agent, or Firm*—Oblon, Fisher, Spivak, McClelland & Maier

[57] ABSTRACT

Methacrylic acid is produced by the vapor phase oxidation of methacrolein in the presence of a complex oxide catalyst having the formula:

$$Mo_aV_bP_cCe_dCu_eX_fO_g$$

wherein X represents at least one of the elements selected from the group of Mn, Fe, Co, Sn and Te and a, b, c, d, e, f and g represent atomic ratios wherein a=12; b=0.01 to 2; c=0.1 to 3; d=0.01 to 2; e=0.01 to 2; f=0 to 2 and g is determined by the valences of the non-oxygen components of the catalyst and is usually in a range of 38 to 50. The catalyst can be optionally reduced by subjecting the metal oxide mixture to at least one reducing organic material selected from the group consisting of dibasic carboxylic acids, oxycarboxylic acids, and polyols.

11 Claims, No Drawings

PROCESS FOR PRODUCING METHACRYLIC ACID

BACKGROUND OF THE INVENTION

1. Field of the Invention

The present invention relates to a process for producing methacrylic acid by the vapor phase catalytic oxidation of methacrolein with molecular oxygen or a molecular oxygen-containing gas. More particularly, it relates to a process for producing methacrylic acid in high yield by the vapor phase catalytic oxidation of methacrolein over a multi-element complex oxide catalyst of Mo, V, P, Ce and Cu. If desired, at least one element selected from the group of Mn, Fe, Co, Sn and Te can also be incorporated in the catalyst. The catalyst containing the optional metal component can also be optionally reduced with a reducing organic material.

2. Description of the Prior Art

Methacrylic acid esters such as methyl methacrylate which are commonly used as starting materials for transparent plastics have been produced by the acetone-cyanohydrin process which employs acetone and hydrogen cyanide. However, the conventional process has several disadvantages in that large amounts of by-products are formed and an expensive procedure is required for the recovery of cyanide and sulfuric acid and hydrogen cyanide, which are the highly toxic starting materials. Moreover, the starting materials are not easily available. Because of these drawbacks, it is highly desirable to develop a new economical and rational process for the industrial synthesis of methacrylic acid esters.

The development of a process for producing methacrylic acid esters from isobutylene as the starting material has been greatly anticipated and desired. A process involves the vapor phase oxidation of isobutylene in the spent B-B fractions to produce methacrolein which in turn is oxidized to methacrylic acid. The acid is finally esterified to a methacrylic acid ester.

Another process for producing acrylic acid esters by the direct oxidation of propylene as the starting material has been conducted in many large plants. However, a similar process for the production of analogous compounds, i.e., methacrylic acid esters, has not been developed on an industrial scale. One of the main reasons for the difficulty encountered in developing a satisfactory procedure is the difficulty of oxidizing methacrolein to methacrylic acid. In practice, even though Mo-V type (and Mo-V-W type) catalysts, which exhibit excellent catalytic activity in the production of acrylic acid from acrolein, have been used for the catalytic oxidation of methacrolein to methacrylic acid, the desired results have not been attained. The single flow yield of methacrylic acid from methacrolein has only been as high as about 10 to 20%. Furthermore, when the Mo-P type catalysts which have been proposed for use in various processes have been used as catalysts for producing methacrylic acid by the vapor phase oxidation of methacrolein, low single flow yields of methacrylic acid have been obtained and the activity of the catalysts has been too low to achieve the desired results on an industrial scale.

With regard to the process for producing methacrylic acid by the vapor phase oxidation of methacrolein with a molecular oxygen or a molecular oxygen-containing gas, many patents have issued which show various Mo-P type catalysts such as Japanese Patent Publication No. 24288/1975, which more specifically shows a catalyst system of Mo, P and Tl containing at least one element from the group of Si, Cr, Al and Ti; Japanese Unexamined Patent Publication No. 96552/1975 which shows a catalyst system of Mo, P and V containing at least one element from the group of Na, K, Rb and Cs; and Japanese Unexamined Patent Publication No. 123619/1975 which shows a catalyst system of Mo, P, V containing at least one element from the group of K, Rb, Cs and Tl, and if desired at least one element from the group of Sr, Zn, Cd, Nb, B, Pb, Bi and W. However, even though an alkali metal, an alkaline earth metal or another metal component has been added as a promoter to the Mo-P type catalysts, as proposed in the prior art, it has been difficult to attain satisfactory results for an industrial scale operation because the promotional effects attributable to the presence of the additional metal component are insufficient. Moreover, the stability of the lifetime characteristics of the catalyst in use is an important and an indispensible industrial factor in addition to catalytic activity and selectivity factors.

Generally, it is known that Mo-P type catalysts possess inferior heat stability at high temperatures which is the cause of substantial losses in catalytic activities, as disclosed in many patents such as Japanese Patent Publication No. 27526/1965 and Japanese Unexamined Patent Publication No. 33082/1972. However, the disadvantages of the Mo-P type catalysts cannot be overcome by the simple addition of an alkali metal or other component to the catalyst because of the substantial characteristics of the Mo-P type catalysts. The reason for this may be that the dehydrating condensation of phosphoric acid and the growth of crystals of molybdenum trioxide occur simultaneously in the catalyst at high temperatures, especially higher than 340° C., which results in a sudden decrease of the surface area and the development of a fine surface pore structure.

An improved catalyst containing Mo, V, P, and Ce which possesses substantially improved catalytic activity has been developed. However, it would be desirable to have a catalyst which possesses high activity at lower temperature (especially about 270° C. to 280° C.).

A study has been conducted and it has been found that Mo-V-P-Ce-Cu type catalysts which contain at least one element of the group of Mn, Fe, Co, Sn and Te have very high catalytic activity at relatively low temperature and the yield of product is further improved by reduction of the catalyst by treating the catalyst with a reducing organic material such as a dibasic carboxylic acid or an oxycarboxylic acid.

Another Mo-P catalyst is known for the conversion of methacrolein to methacrylic acid as disclosed in U.S. Pat. No. 3,875,220. The catalyst in addition to Mo and P optionally contains one or more elements of the group of bismuth, arsenic, boron, cerium, chromium, silver, iron, tungsten, nickel, niobium, lead, manganese, thallium, tellurium, tin or copper. However, cerium and copper are not essential components of the catalyst, while these elements are essential components of the present catalyst. Moreover, it has been found experimentally that the improved results of the present invention can only be obtained with the present catalyst having the components specified.

SUMMARY OF THE INVENTION

One object of the present invention is to provide a process for producing methacrylic acid by the vapor phase oxidation of methacrolein in high yield and high selectivity.

Another object of the invention is to provide a process for producing methacrylic acid by the vapor phase oxidation of methacrolein over a catalyst having high activity at relatively low temperature.

Briefly, these objects and other objects as hereinafter will become more readily apparent can be attained by a process for producing methacrylic acid by the vapor phase oxidation of methacrolein in the presence of a complex oxide catalyst having the formula:

$$Mo_aV_bP_cCe_dCu_eX_fO_g$$

wherein X represents at least one element from the group of Mn, Fe, Co, Sn and Te and a, b, c, d, e, f and g represent atomic ratios wherein a=12; b=0.01 to 2; c=0.1 to 3; d=0.01 to 2; e=0.01 to 2; f=0 to 2 and g is determined by the valences of the non-oxygen components of the catalyst and is usually in the range of 38 to 50. The mixed metal oxides can optionally be subjected to reduction with at least one reducing organic material selected from the group consisting of dibasic carboxylic acids, oxycarboxylic acids, and polyols.

DETAILED DESCRIPTION OF THE PREFERRED EMBODIMENTS

The process of the present invention can be conducted at relatively low temperatures such as from 270° to 280° C. Because of the lower temperatures used, the activity of the catalyst can be stably maintained for long times. Moreover, methacrylic acid can be economically produced in high space time yields thereby being very attractive industrially.

As will become clear from a comparison of the present catalyst with reference catalysts, the catalyst of the present invention contains Mo, V, P, Ce and Cu (oxides) as indispensible components. If one of these components is not present, the single flow yield of methacrylic acid (or space time yield) is very low, or the operation becomes industrially unsatisfactory.

The catalyst of the invention is effective when the components are present in the above-mentioned quantities. An especially excellent activity can be obtained by using a complex oxide catalyst having the formula:

$$M_aV_bP_cCe_dCu_eX_fO_g$$

wherein a=12; b=0.1 to 1.0; c=1.0 to 2.5; d=0.02 to 0.8; e=0.1 to 1.0; f=0.1 to 1.0 and g is determined by the valences of the non-oxygen components of the catalyst and is usually 38 to 50.

A catalyst of superior activity can be obtained by subjecting the mixed metal oxides to reduction with a reducing organic material of a dicarboxylic acid such as oxalic acid or succinic acid; an oxycarboxylic acid such as tartaric acid, lactic acid or citric acid; or a polyol such as mannitol or pyrogallol. The amount of the reducing organic material employed is usually within the range of 5 to 40 wt.%, preferably 10 to 20 wt.%, based on the amount of complex oxides in the catalyst.

The catalyst of the present invention can be produced by any conventional desired method, and is usually prepared by a precipitation-concentrating method or an impregnation-supporting method or the like.

The complex oxide catalyst can be used without a carrier. However, it can be supported on a carrier by impregnating a desired preshaped carrier, preferably having a surface area of 2 to 3 m²/g or smaller with large size pores, such as α-alumina, silica, alumina, silicon-carbide, titanium oxide, magnesium oxide or the like with the mixed metal oxides. The catalyst may also be mixed and molded with a powder such as diatomaceous earth, kaolin, zirconia, silicon carbide or the like. The support has the advantage of promoting the dissipation of the heat of reaction, thereby inhibiting the degrative oxidation of the product methacrylic acid. Moreover, the mechanical strength of the catalyst is improved.

The starting materials for the elements of the catalysts of the present invention preferably are usually water soluble compounds such as nitrates and ammonium salts, and can be chlorides, hydroxides, sulfates and the like. However, these salts are not critical. Suitable sources of molybdenum include para-ammonium molybdate, molybdic acid, and the like. Suitable sources of vanadium include ammonium metavanadate, vanadium pentoxide, vanadium oxydichloride, vanadium trichloride, vanadium trioxide, and the like. Suitable sources of phosphorous include phosphoric acid, ammonium phosphate and the like. Suitable sources of cerium include cerium nitrate, ammonium cerium nitrate, and the like. Suitable sources of copper include cupric nitrate, cuprous chloride, cupric chloride, and the like. Suitable sources of manganese include manganese nitrate and the like. Suitable sources of iron include ferric nitrate, ferrous chloride, ferric chloride, and the like. Suitable sources of cobalt include cobalt nitrate, and the like. Suitable sources of tin include stannous chloride, stannic chloride, and the like. Suitable sources of tellurium include tellurium dioxide and the like.

The catalysts of the invention can be prepared without a special heat treatment, however it is preferable to dry the composition of the above-mentioned components at 100° to 200° C. for several hours to several tens of hours and then to calcine the composition at 300° to 450° C., preferably 350° to 400° C. in air or a feed gas for several hours up to and in excess of ten hours. It is preferable not to calcine the catalyst at a temperature higher than 450° C. for a long time, because such a treatment results in substantial loss of catalytic activity. In the operation of the invention, the catalyst is usually used in a fixed bed, but it can also be used in a fluidized bed.

The feed gas comprises methacrolein and molecular oxygen, and if desired a diluent gas such as steam, air, nitrogen, carbon dioxide or the like.

It is possible to use a methacrolein-containing gas produced by the catalytic vapor phase oxidation of isobutylene without condensation as the methacrolein source. Even if small amounts of carbon dioxide, carbon monoxide, unreacted isobutylene and other impurities such as n-butenes, butanes and the like are present, the reaction is not detrimentally influenced by these substances.

The reaction can be conducted at temperatures ranging from 240° to 380° C., preferably ranging from 260° to 320° C. Although, the apparent contact time varies according to the composition of the catalyst, the reaction temperature and the other conditions, it is usually in a range of 0.5 to 6 seconds, especially 1 to 4 seconds. The composition of the feed gas can be selected from a broad range and it is unnecessary to define specific concentrations for methacrolein and oxygen. Preferably, the feed gas contains 1 to 7 vol. % methacrolein, 50–90 vol. % air and 5 to 50 vol. % steam. The resulting methacrylic acid can be separated from the reaction mixture by the conventional methods such as by solvent extraction. The unreacted methacrolein can be separated and recovered, and used again as the starting material.

Having generally described the invention, a more complete understanding can be obtained by reference to certain specific examples, which are provided herein for purposes of illustration only and are not intended to be limiting unless otherwise specified.

The following definitions apply to the coversion of methacrolein, the selectivities for methacrylic acid and acetic acid and the single flow yield of methacrylic acid.

Conversion of Methacrolein (%) =

$$\frac{\text{moles of methacrolein reacted}}{\text{moles of methacrolein fed}} \times 100$$

Selectivity (%) =

$$\frac{\text{moles of each product} \times \frac{\text{carbon number of each product}}{4}}{\text{moles of methacrolein reacted}} \times 100$$

Single Flow yield of methacrylic acid (%) =

$$\frac{\text{moles of methacrylic acid produced}}{\text{moles of methacrolein fed}} \times 100$$

The results of experiments using the catalyst of this invention are shown in the following examples as well as a number of comparative examples. The experiments were conducted using the following experimental procedure. A 16 g amount of a catalyst was placed in a Pyrex glass fixed bed reaction column having an inner diameter of 20 mm. The reaction column was heated in an electric tubular furnace, and a feed gas containing about 5 vol. % of methacrolein, about 60 vol. % of air and about 35 vol. % of steam was passed through the column at 2 seconds of apparent contact time at a constant reaction temperature in the range of 260° C. to 320° C. usually 280° C.

The life-time test was performed by the following experimental procedure.

A stainless steel U-shaped column having an inner diameter of 25 mm was filled with 40 g of a catalyst. The U-shaped column was dipped into a molten salt bath and the feed gas having the same components was continuously fed through the U-shaped column at the reaction temperature of 280° C. and a space velocity of 1,800 hr$^{-1}$. The reaction products were analyzed by neutralization titration and gas chromatography.

EXAMPLE 1

In 200 ml of distilled water heated at about 80° C. in a hot water bath were dissolved 106.0 g of ammonium paramolybdenate and 3.5 g of ammonium metavanadate. The solution was admixed with 50 ml of an aqueous solution containing 13.2 g of ammonium phosphate(dibasic) while heated and stirred. The mixture was admixed with 100 ml of an aqueous solution containing 4.3 g of cerium nitrate and 2.0 g of cuprous chloride and the mixture was concentrated with stirring. Then, 11 g of diatomaceous earth was added to the concentrated mixture. The mixture was molded in the form of pellets having a diameter of 5 mm. The pellets were dried in an oven for about 20 hours, calcined at 300° C. for 4 hours in air and then sintered at 380° C. for 6 hours whereby a catalyst was obtained.

The catalyst obtained has the formula:

$$Mo_{12}V_{0.6}P_2Ce_{0.2}Cu_{0.4}$$

with oxygen excluded. The catalyst was supported on 10 wt.% of diatomaceous earth.

The reaction was conducted by oxidizing methacrolein with air at 280° C. for an apparent contact time (residence time) of 2 seconds. As a result, the conversion of methacrolein was 86.2%, the selectivity of methacrylic acid was 73.7% and the single flow yield of methacrylic acid was 63.5%.

EXAMPLES 2 to 21, REFERENCES 1 to 9

The process of Example 1 was followed to prepare various catalysts, and the reaction of methacrolein was conducted at 280° C. for an apparent time (residence time) of 2 seconds.

The results are shown in Table 1.

TABLE 1

| | Atomic Ratios Of Catalyst Components (oxygen excluded) | | | | | Conversion of Methacrolein (%) | Selectivity to Methacrylic acid (%) | Single Flow Yield of Methacrylic acid (%) |
|---|---|---|---|---|---|---|---|---|
| | Mo | V | P | Ce | Cu | X | | | |
| Exp. 2 | 12 | 0.6 | 2.0 | 0.2 | 0.2 | — | 78.6 | 80.9 | 63.6 |
| Exp. 3 | 12 | 0.6 | 2.0 | 0.2 | 0.8 | — | 79.1 | 74.3 | 58.8 |
| Exp. 4 | 12 | 0.6 | 2.0 | 0.2 | 2.0 | — | 64.6 | 71.9 | 46.6 |
| Ref. 1 | 12 | 0.6 | 2.0 | 0.2 | 2.4 | — | 46.7 | 67.0 | 31.3 |
| Ref. 2 | 12 | 0.6 | 2.0 | 0.2 | 0 | — | 52.3 | 80.6 | 42.2 |
| Exp. 5 | 12 | 0.6 | 2.0 | 0.06 | 0.4 | — | 62.4 | 78.6 | 49.0 |
| Exp. 6 | 12 | 0.6 | 2.0 | 0.4 | 0.4 | — | 87.3 | 72.0 | 62.9 |
| Exp. 7 | 12 | 0.6 | 2.0 | 0.8 | 0.4 | — | 68.0 | 73.1 | 49.7 |
| Exp. 8 | 12 | 0.6 | 2.0 | 2.0 | 0.4 | — | 59.8 | 74.4 | 44.5 |
| Ref. 3 | 12 | 0.6 | 2.0 | 2.4 | 0.4 | — | 52.7 | 68.9 | 36.3 |
| Ref. 4 | 12 | 0.6 | 2.0 | 0 | 0.4 | — | 37.0 | 68.2 | 25.2 |
| Exp. 9 | 12 | 0.6 | 1.0 | 0.2 | 0.4 | — | 67.2 | 73.8 | 49.6 |
| Exp. 10 | 12 | 0.6 | 1.8 | 0.2 | 0.4 | — | 77.8 | 78.1 | 60.8 |
| Exp. 11 | 12 | 0.6 | 3.0 | 0.2 | 0.4 | — | 60.5 | 79.0 | 47.8 |
| Ref. 5 | 12 | 0.6 | 4.0 | 0.3 | 0.4 | — | 45.4 | 78.8 | 35.8 |
| Exp. 12 | 12 | 0.3 | 2.0 | 0.2 | 0.4 | — | 74.9 | 76.4 | 57.2 |
| Exp. 13 | 12 | 1.0 | 2.0 | 0.2 | 0.4 | — | 78.5 | 74.8 | 58.7 |
| Exp. 14 | 12 | 2.0 | 2.0 | 0.2 | 0.4 | — | 65.5 | 72.1 | 47.2 |
| Ref. 6 | 12 | 2.4 | 2.0 | 0.3 | 0.4 | — | 53.2 | 65.1 | 34.6 |
| Exp. 15 | 12 | 0.6 | 2.0 | 0.2 | 0.4 | Mn$_{0.4}$ | 86.7 | 74.7 | 64.8 |
| Exp. 16 | 12 | 0.6 | 2.0 | 0.2 | 0.4 | Co$_{0.4}$ | 87.4 | 75.8 | 66.2 |

TABLE 1-continued

| | Atomic Ratios Of Catalyst Components (oxygen excluded) | | | | | Conversion of Metha-crolein (%) | Selectivity to Metha-crylic acid (%) | Single Flow Yield of Metha-crylic acid (%) |
|---|---|---|---|---|---|---|---|---|
| | Mo | V | P | Ce | Cu | X | | | |
| Exp. 17 | 12 | 0.6 | 2.0 | 0.2 | 0.4 | Te$_{0.4}$ | 82.1 | 78.6 | 64.5 |
| Exp. 18 | 12 | 0.6 | 2.0 | 0.2 | 0.4 | Fe$_{0.4}$ | 89.2 | 72.9 | 65.0 |
| Exp. 19 | 12 | 0.6 | 2.0 | 0.2 | 0.4 | Sn$_{0.4}$ | 90.3 | 71.6 | 64.7 |
| Exp. 20 | 12 | 0.7 | 2.0 | 0.3 | 0.4 | Fe$_{0.2}$Sn$_{0.2}$ | 89.7 | 71.0 | 63.7 |
| Exp. 21 | 12 | 0.7 | 2.0 | 0.3 | 0.3 | Sn$_{0.3}$Te$_{0.2}$ | 85.4 | 75.2 | 64.2 |
| Ref. 7 | 12 | 0.7 | 2.0 | 0 | 0.4 | Fe$_{0.2}$Sn$_{0.2}$ | 44.3 | 63.8 | 28.3 |
| Ref. 8 | 12 | 0 | 2.0 | 0 | 0.4 | Fe$_{0.2}$Sn$_{0.2}$ | 42.6 | 67.4 | 28.7 |
| Ref. 9 | 12 | 1.0 | 0 | 0.2 | 0.4 | Mn$_{0.4}$ | 33.7 | 6.7 | 2.3 |

EXAMPLE 22

In 200 ml of distilled water heated at about 80° C. was dissolved 106.0 g of ammonium paramolybdenate (NH$_4$)$_6$Mo$_7$O$_{24}$.4H$_2$O. The solution was admixed with 50 ml of an aqueous solution containing 13.2 g of ammonium phosphate (dibasic) (NH$_4$)$_2$HPO$_4$ while heated and stirred.

In 100 ml of distilled water heated at about 80° C. was dissolved 35 g of ammonium metavanadate NH$_4$VO$_3$. A 10 g amount of oxalic acid H$_2$C$_2$O$_4$.2H$_2$O was admixed with the solution while heated and stirred. The amount of oxalic acid employed in relation to the oxide components of the catalyst was 10 wt.%. The resulting aqueous solution was admixed with the former aqueous solution and then a 50 ml amount of an aqueous solution containing 4.3 g of cerium nitrate Ce(NO$_3$)$_3$.6H$_2$O and a 50 ml amount of an aqueous solution containing 4.8 g of cupric nitrate Cu(NO$_3$)$_2$.3H$_2$O were added to the mixed solution. The resulting mixture was heated with stirring on a hot water bath. An 11 g amount of diatomaceous earth was admixed as a support. The resulting slurry was concentrated and the residue was molded in the form of pellets having a diameter of 5 mm. The pellets were dried at 160° C. for about 20 hours, calcined at 300° C. for 4 hours in air and then sintered at 380° C. for 6 hours whereby a catalyst was obtained.

The catalyst obtained has the formula:

$$Mo_{12}V_{0.6}P_2Ce_{0.2}Cu_{0.4}$$

with oxygen excluded. The catalyst was supported on 10 wt.% of diatomaceous earth.

The reaction was conducted by oxidizing methacrolein with air over 16 g of the catalyst packed in a reaction column at 280° C. for an apparent contact time (residence time) of 2 seconds.

As a result, the conversion of methacrolein was 90.7%, the selectivity of methacrylic acid was 76.4% and the single flow yield of methacrylic acid was 69.3%. The selectivities to acetic acid, carbon monoxide and carbon dioxide were 6.7%, 7.2% and 8.6% respectively. When the same reaction was conducted at 300° C. for an apparent contact time (residence time) of 2 seconds, the conversion of methacrolein was 97.4%, the selectivity of methacrylic acid was 70.2% and the single flow yield of methacrylic acid was 68.4%.

REFERENCE 10

The process of Example 22 was followed except that the copper component was not included. A catalyst was obtained which has the formula:

$$Mo_{12}V_{0.6}P_2Ce_{0.2}$$

with oxygen excluded. The catalyst was supported on 10 wt.% of diatomaceous earth, and the reaction was conducted over a catalyst at 280° C. for an apparent contact time (residence time) of 2 seconds.

As a result, the conversion of methacrolein was 64.5%, the selectivity of methacrylic acid was 82.1% and the single flow yield of methacrylic acid was 53.0%. The selectivities to acetic acid, carbon monoxide and carbon dioxide were 3.7%, 5.1% and 5.9% respectively.

When the same reaction was conducted at 300° C. for an apparent contact time (residence time) of 2 seconds, the conversion of methacrolein was 74.5%, the selectivity of methacrylic acid was 78.7% with a single flow yield of methacrylic acid of 58.6%.

EXAMPLE 23

The process of Example 22 was followed except that 2.0 g of cuprous chloride CuCl and 8.0 g of ferric nitrate Fe(NO$_3$)$_3$.9H$_2$O were added instead of 4.8 g of cupric nitrate. Furthermore, a 17.8 g amount of kaolin was used instead of 11 g of diatomaceous earth. A catalyst was obtained which has the formula:

$$Mo_{12}V_{0.6}P_2Ce_{0.2}Cu_{0.4}Fe_{0.4}$$

with oxygen excluded. The catalyst contained 15 wt.% of kaolin. The reaction of methacrolein was conducted at 280° C. for an apparent contact time (residence time) of 2 seconds. As a result, the conversion of methacrolein was 94.7%, the selectivity of methacrylic acid was 73.6% and the single flow yield of methacrylic acid was 70.4%. The selectivities to acetic acid, carbon monoxide and carbon dioxide were 7.1%, 7.8% and 9.3% respectively.

When the same reaction was conducted at 270° C. for an apparent contact time (residence time) of 2 seconds, the conversion of methacrolein was 88.7%, the selectivity of methacrylic acid was 78.0% and the single flow yield of methacrylic acid was 69.2%.

REFERENCE 11

The process of Example 23 was followed except that the cerium component was not included. A catalyst was obtained which has the formula:

$$Mo_{12}V_{0.6}P_2Cu_{0.4}Fe_{0.4}$$

with oxygen excluded. The catalyst was supported on 15 wt.% kaolin. The reaction of methacrolein was conducted over a catalyst at 280° C. for an apparent contact time (residence time) of 2 seconds. As a result, the conversion of methacrolein was 46.8%, the selectivity of methacrylic acid was 67.1% and the single flow yield of methacrylic acid was 31.4%. When the same reaction was conducted at 300° C. for an apparent contact time (residence time) of 2 seconds, the conversion of methacrolein was 62.3%, the selectivity of methacrylic acid was 57.2% and the single flow yield of methacrylic acid was 35.6%.

EXAMPLE 24

The process of Example 22 was followed except that 3.6 g of cupric nitrate and 4.3 g of manganese nitrate Mn(NO$_3$)$_2$.6H$_2$O were used instead of 4.8 g of cupric nitrate. A catalyst was obtained which has the formula:

$$Mo_{12}V_{0.6}P_2Ce_{0.2}Cu_{0.3}Mn_{0.3}$$

with oxygen excluded. The catalyst was supported on 10 wt.% of diatomaceous earth. The reaction of methacrolein was conducted at 280° C. for an apparent contact time (residence time) of 2 seconds. As a result, the conversion of methacrolein was 93.4%, the selectivity of methacrylic acid was 75.8% and the single flow yield of methacrylic acid was 70.8%.

EXAMPLES 25 to 37, REFERENCE EXAMPLES 12 to 17

The process of Example 22 was followed except that tartaric acid HOOCCH(OH)CH(OH)COOH was used instead of oxalic acid as the reducing organic material. The amounts of the Ce, P, V and Cu components were varied in the production of the catalysts. The reaction of methacrolein was conducted over each catalyst at 280° C. for an apparent contact time (residence time) of 2 seconds.

The results are shown in Table 2.

TABLE 2

|  | Atomic Ratios of Catalyst Components (oxygen excluded) | | | | | Conversion of Methacrolein | Selectivity to Methacrylic acid | Single Flow Yield of Methacrylic Acid |
|---|---|---|---|---|---|---|---|---|
|  | Mo | V | P | Ce | Cu | (%) | (%) | (%) |
| Exp.25 | 12 | 0.6 | 2.0 | 0.06 | 0.4 | 72.1 | 82.7 | 59.6 |
| Exp.26 | 12 | 0.6 | 2.0 | 0.2 | 0.4 | 89.1 | 78.9 | 70.3 |
| Exp.27 | 12 | 0.6 | 2.0 | 0.8 | 0.4 | 75.2 | 74.5 | 56.0 |
| Exp.28 | 12 | 0.6 | 2.0 | 2.0 | 0.4 | 67.4 | 72.3 | 48.7 |
| Ref.12 | 12 | 0.6 | 2.0 | 3.0 | 0.4 | 54.1 | 70.7 | 38.2 |
| Exp.29 | 12 | 0.6 | 1.0 | 0.2 | 0.4 | 76.8 | 74.0 | 56.8 |
| Exp.30 | 12 | 0.6 | 1.8 | 0.2 | 0.4 | 87.7 | 79.2 | 69.5 |
| Exp.31 | 12 | 0.6 | 3.0 | 0.2 | 0.4 | 73.7 | 78.5 | 57.9 |
| Ref.13 | 12 | 0.6 | 4.0 | 0.2 | 0.4 | 57.6 | 76.1 | 43.8 |
| Ref.14 | 12 | 0.6 | 0 | 0.2 | 0.4 | 31.2 | 5.7 | 1.8 |
| Exp.32 | 12 | 0.3 | 2.0 | 0.2 | 0.4 | 83.5 | 80.9 | 67.6 |
| Exp.33 | 12 | 1.0 | 2.0 | 0.2 | 0.4 | 86.1 | 76.6 | 66.0 |
| Exp.34 | 12 | 2.0 | 2.0 | 0.2 | 0.4 | 77.4 | 74.0 | 57.3 |
| Ref.15 | 12 | 3.0 | 2.0 | 0.2 | 0.4 | 59.0 | 71.3 | 42.1 |
| Ref.16 | 12 | 0 | 2.0 | 0.2 | 0.4 | 45.9 | 69.4 | 31.9 |
| Exp.35 | 12 | 0.6 | 2.0 | 0.2 | 0.7 | 89.7 | 75.0 | 67.3 |
| Exp.36 | 12 | 0.6 | 2.0 | 0.2 | 1.0 | 84.6 | 73.9 | 62.5 |
| Exp.37 | 12 | 0.6 | 2.0 | 0.2 | 2.0 | 75.1 | 74.5 | 55.9 |
| Ref.17 | 12 | 0.6 | 2.0 | 0.2 | 3.0 | 62.2 | 65.4 | 40.7 |

EXAMPLES 38 to 46

The process of Example 22 was followed except that a mixture of 2.0 g of cuprous chloride and 5.7 g of manganese nitrate or a mixture of 8.0 g of ferric nitrate, 5.8 g of cobalt nitrate Co(NO$_3$)$_2$.6H$_2$O, 4.5 g of stannous chloride SnCl$_2$ and tellurium dioxide TeO$_2$ was used instead of 4.8 g of cupric nitrate. Catalysts were obtained which have the formula:

$$Mo_{12}V_{0.6}P_2Ce_{0.2}Cu_{0.4}X_{0.4}$$

with oxygen excluded, wherein X=Mn, Fe, Co, Sn or Te. The catalysts were supported on 10 wt.% of diatomaceous earth. By the same method catalysts having Mo, V, P, Ce and Cu components and two or more components of Mn, Fe, Co, Sn and Te were also produced.

The process of Example 22 was followed for the reaction of methacrolein over each catalyst at 280° C. for an apparent contact time (residence time) of 2 seconds.

The results are shown in Table 3.

TABLE 3

|  | Atomic Ratios of Catalyst Components (except oxygen) | | | | | | Conversion of methacrolein | Selectivity to methacrylic acid | Single flow yield of methacrylic acid |
|---|---|---|---|---|---|---|---|---|---|
|  | Mo | V | P | Ce | Cu | X | (%) | (%) | (%) |
| Exp.38 | 12 | 0.6 | 2.0 | 0.2 | 0.4 | Mn$_{0.4}$ | 97.2 | 72.5 | 70.5 |
| Exp.39 | 12 | 0.6 | 2.0 | 0.2 | 0.4 | Fe$_{0.4}$ | 96.4 | 72.3 | 69.7 |
| Exp.40 | 12 | 0.6 | 2.0 | 0.2 | 0.4 | Co$_{0.4}$ | 94.2 | 74.1 | 69.8 |
| Exp.41 | 12 | 0.6 | 2.0 | 0.2 | 0.4 | Sn$_{0.4}$ | 97.1 | 72.2 | 70.1 |
| Exp.42 | 12 | 0.6 | 2.0 | 0.2 | 0.4 | Te$_{0.4}$ | 92.8 | 76.9 | 71.4 |
| Exp.43 | 12 | 0.6 | 2.0 | 0.2 | 0.3 | Mn$_{0.3}$Co$_{0.3}$ | 94.3 | 73.8 | 69.6 |
| Exp.44 | 12 | 0.7 | 2.0 | 0.3 | 0.3 | Sn$_{0.3}$Te$_{0.2}$ | 96.7 | 74.7 | 72.2 |
| Exp.45 | 12 | 0.7 | 2.0 | 0.3 | 0.4 | Fe$_{0.2}$Sn$_{0.2}$ | 95.7 | 72.8 | 69.7 |

TABLE 3-continued

| | Atomic Ratios of Catalyst Components (except oxygen) | | | | | Conversion of methacrolein (%) | Selectivity to methacrylic acid (%) | Single flow yield of methacrylic acid (%) |
|---|---|---|---|---|---|---|---|---|
| | Mo | V | P | Ce | Cu | X | | |
| Exp.46 | 12 | 0.7 | 2.0 | 0.2 | 0.2 | $Mn_{0.2}Fe_{0.2}Te_{0.2}$ | 94.5 | 73.5 | 69.5 |

EXAMPLES 47 to 53

The process of Example 24 was followed except that the types and the amounts of the reducing organic material were varied. Catalysts were obtained which have the formula:

$$Mo_{12}V_{0.6}P_2Ce_{0.2}Cu_{0.3}Mn_{0.3}$$

with oxygen excluded. The catalysts were supported on 10 wt.% of diatomaceous earth. The reaction of methacrolein was conducted over each catalyst at 280° C. for an apparent contact time (residence time) of 2 seconds.
The results are shown in Table 4.

TABLE 4

| | Type of reducing organic material | Amount of organic material (based on the oxides) (wt. %) | Conversion of Methacrolein (%) | Selectivity to Methacrylic acid (%) | Single Flow yield of Methacrylic Acid (%) |
|---|---|---|---|---|---|
| Exp.47 | none | 0 | 87.5 | 74.2 | 64.9 |
| Exp.24 | oxalic acid | 10 | 93.4 | 75.8 | 70.8 |
| Exp.48 | oxalic acid | 20 | 94.8 | 73.1 | 69.3 |
| Exp.49 | oxalic acid | 40 | 88.5 | 70.5 | 62.4 |
| Exp.40 | succinic acid | 10 | 90.8 | 77.3 | 70.2 |
| Exp.51 | citric acid | 10 | 91.9 | 74.0 | 68.0 |
| Exp.52 | pyrogallol | 10 | 96.1 | 71.2 | 68.4 |
| Exp.53 | mannitol | 10 | 86.2 | 76.1 | 65.6 |

EXAMPLE 54

The process of Example 23 was followed except that 236 g of α-alumina support molded in the form of pellets having a diameter of 6 mm was used instead of 17.8 g of kaolin. The mixture was heated with stirring and concentrated to support the catalyst. A catalyst was obtained which has the formula:

$$Mo_{12}V_{0.6}P_2Ce_{0.2}Cu_{0.4}Fe_{0.4}$$

with oxygen excluded. The catalyst was supported on $\alpha$-$Al_2O_3$, i.e., 30 wt.% based on the amount of the catalyst. The reaction of methacrolein was conducted over the catalyst at 280° C. for an apparent contact time (residence time) of 3 seconds. As a result, the conversion of methacrolein was 77.8%, the selectivity of methacrylic acid was 82.9% and the single flow yield of methacrylic acid was 64.5%.

EXAMPLE 55

A life-time test of the catalyst of Example 23 which has the formula:

$$Mo_{12}V_{0.6}P_2Cu_{0.4}Fe_{0.4}$$

with oxygen excluded was conducted. The catalyst was supported on 15 wt.% of kaolin, and the reaction was conducted at a reaction temperature of 280° C. and a space velocity of about 1800.

A life-time test of the catalyst of Reference 10 which has the formula:

$$Mo_{12}V_{0.6}P_2Ce_{0.2}$$

with oxygen excluded was conducted. The catalyst was supported on 10 wt.% of diatomaceous earth, and the reaction was conducted at a reaction temperature of 340° C. and a space velocity of about 1800.

The results are shown in Table 5.

It was found that the catalyst of the invention exhibited a very high and stable catalytic activity at relatively low temperature.

TABLE 5

| Catalyst | Conditions of the Reaction | | Term of Operation (days) | Conversion of methacrolein (%) | Selectivity to methacrylic acid (%) | Single flow yield of methacrylic acid (%) |
|---|---|---|---|---|---|---|
| | Reaction Temp. | Temp. of bath | | | | |
| *1 | 280° C. | 262° C. | 2 | 92.4 | 72.9 | 67.4 |
| " | " | " | 20 | 91.0 | 74.6 | 67.0 |
| " | " | 265° C. | 40 | 93.7 | 72.5 | 67.9 |
| " | " | " | 60 | 92.5 | 73.7 | 68.2 |
| " | " | " | 90 | 91.8 | 73.0 | 67.0 |
| *2 | 340° C. | 327° C. | 2 | 95.5 | 67.7 | 64.7 |
| " | " | 330° C. | 20 | 86.1 | 65.0 | 56.0 |
| " | " | 334° C. | 40 | 72.1 | 62.4 | 45.0 |

*1 $Mo_{12}V_{0.6}P_2Ce_{0.2}Cu_{0.4}Fe_{0.4}$ ; kaolin 15 weight percent
*2 $Mo_{12}V_{0.6}P_2Ce_{0.2}$ . diatomaceous earth 10 weight percent

Having now fully described the invention, it will be apparent to one of ordinary skill in the art that many changes and modifications can be made thereto without departing from the spirit or scope of the invention as set forth herein.

What is claimed as new and intended to be secured by Letters Patent is:

1. A process for producing methacrylic acid, which comprises:
   reacting methacrolein with molecular oxygen or a molecular oxygen-containing gas in the vapor phase in the presence of a complex oxide catalyst having the formula:

$$Mo_aV_bP_cCe_dCu_eX_fO_g$$

wherein X represents at least one element selected from the group consisting of manganese, iron, cobalt, tin and tellurium and wherein a, b, c, d, e and f represent atomic ratios such that when a=12; b=0.01 to 2; c=0.1 to 3; d=0.01 to 2; e=0.01 to 2; f=0 to 2 and g assumes a value depending upon the valences of the other components in the range of 38 to 50.

2. The process of claim 1, wherein the elemental atomic ratios of said empirical formula are a=12, b=0.1 to 1.0, c=1.0 to 2.5, d=0.02 to 0.8, e=0.1 to 1.0; f=0.1 to 1.0 and g assumes a value depending upon the valences of the other components in the range of 38 to 50.

3. The process of claim 1, wherein the catalyst is prepared by the addition of a reducing organic material to the components from which said catalyst is formed selected from the group consisting of dibasic carboxylic acids, oxycarboxylic acids and polyols.

4. The process of claim 3, wherein said reducing organic material is selected from the group consisting of oxalic acid, succinic acid, tartaric acid, citric acid, lactic acid, mannitol and pyrogallol.

5. The process of claim 1, wherein the catalyst is supported on a carrier.

6. The process of claim 1, wherein the catalyst is calcined at a temperature in the range of 300° to 450° C.

7. The process of claim 1, wherein said oxidation of methacrolein is conducted at a temperature in the range of 240° to 380° C.

8. The process of claim 1, wherein said oxidation of methacrolein is conducted at an apparent contact time in the range of 1 to 4 seconds.

9. The process according to claim 1, wherein molecular oxygen or molecular oxygen-containing gas is supplied in the form of air.

10. The process according to claim 1, wherein the feed gas comprises a reaction gas mixture prepared by oxidizing isobutylene.

11. The process according to claim 1, wherein said oxidation of methacrolein is conducted in the presence of an inert gaseous diluent which is selected from the group consisting of steam, nitrogen and carbon dioxide.

* * * * *